United States Patent [19]

Baldwin et al.

[11] Patent Number: 4,486,446

[45] Date of Patent: Dec. 4, 1984

[54] ARALKYLAMINOETHANOL HETEROCYCLIC COMPOUNDS

[75] Inventors: John J. Baldwin, Gwynedd Valley; David E. McClure, Lansdale, both of Pa.

[73] Assignee: Merck & Co., Inc., Rahway, N.J.

[21] Appl. No.: 219,764

[22] Filed: Dec. 23, 1980

[51] Int. Cl.$^3$ .............................................. A61K 31/35
[52] U.S. Cl. ..................................... 424/283; 549/417
[58] Field of Search ................... 260/345.9 R; 424/283

[56] References Cited

U.S. PATENT DOCUMENTS 3,644,353 2/1972 Lunt et al. ........................... 544/162
3,705,233 12/1972 Lunt ...................................... 424/45

FOREIGN PATENT DOCUMENTS 978958 12/1975 Canada ........................ 260/345.9 R

*Primary Examiner*—Nicky Chan
*Attorney, Agent, or Firm*—Alice O. Robertson; Daniel T. Szura

[57] ABSTRACT

Heterocyclicaminoethanols of the formula

Het—CHOH—CH$_2$—NH—aralkyl where Het is a pyrone ring are disclosed. The compounds are useful as pharmaceuticals.

8 Claims, No Drawings

ARALKYLAMINOETHANOL HETEROCYCLIC COMPOUNDS

BACKGROUND OF THE INVENTION

The present invention is concerned with heterocyclic compounds of the formula HET—CHOH—CH$_2$—NH—aralkyl, where Het is a pyrone ring.

Substituted phenylaminoethanols of the formula Ph—CHOH—CH$_2$—NH—aralkyl where Ph is a substituted phenolic group are disclosed in U.S. Pat. No. 3,644,353; U.S. Pat. No. 3,705,233. These compounds have random activity as β-adrenergic stimulants and β-adrenergic blockers. These compounds are taught to be useful as pharmaceuticals for treating glaucoma and cardiovascular disorders such as hypertension and arrhythmias.

Heterocyclic aminoethanols which have pharmaceutical utility have been discovered.

SUMMARY OF THE INVENTION

Heterocyclic compounds of the formula HET—CHOH—CH$_2$—NH—aralkyl where HET is 6membered O-heterocyclic and their use as pharmaceuticals.

DESCRIPTION OF THE PREFERRED EMBODIMENTS

An embodiment of the present invention is compounds of the formula

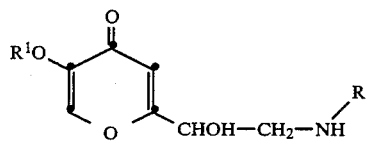

I individual isomers, tautomers thereof, and pharmaceutically acceptable salts thereof wherein
R$^1$ is H, CH$_3$ or —CH$_2$—phenyl and
R is

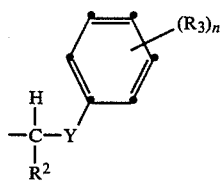

wherein
R$^2$ is selected from H and C$_1$-C$_3$alkyl,
Y is CH$_2$, (CH$_2$)$_2$, or —CH$_2$O—
R$_3$ is H, OH, O—C$_{1-3}$alkyl, halogen C$_{1-3}$alkyl or methylenedioxy and
n is 1 or 2.

The pharmaceutically acceptable salts are the salts of the Formula I base with suitable organic or inorganic acids. Suitable organic acids include carboxylic acids such as acetic acid, pamoic acid, pivalic acid, oxalic acid, lauric acid, pelargonic acid, citric acid, tartaric acid, maleic acid, oleic acid, propanoic acid, succinic acid, isobutyric acid, malic acid and the like, the noncarboxylic acids such as isethionic acid and methane sulfonic acid. Maleic acid salts are preferred. Suitable inorganic acids are the hydrogen halides, e.g., HCl, HI, HBr, phosphoric acid and sulfuric acid. The hydrohalide salts, and especially the hydrochlorides, are preferred. These salts can be prepared by treating the free base with an appropriate amount of a suitable acid, generally in a solvent.

R is the phenalkyl group

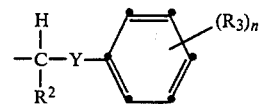

R$^2$ may be C$_1$-C$_3$alkyl e.g. CH$_3$, C$_3$H$_7$, C$_2$H$_5$ and the like, or hydrogen. CH$_3$ and H are preferred substituents while it is more preferred when R$^2$ is CH$_3$. Y is CH$_2$O, CH$_2$ or —(CH$_2$)—$_2$ with CH$_2$ and (CH$_2$)$_2$ being preferred. R$_3$ is H, OH, O—C$_1$-C$_3$alkyl, halogen (Br, Cl, I or F with Br and Cl being preferred) and C$_1$-C$_3$-alkyl, branched or linear. H and OCH$_3$ are preferred definitions of R$_3$.

Examples illustrating useful R$_3$ groups are:

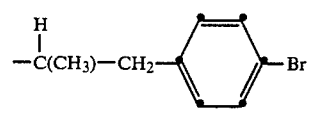

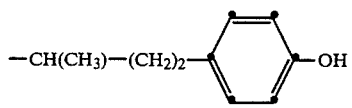

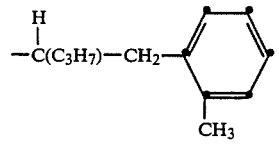

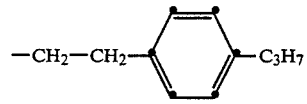

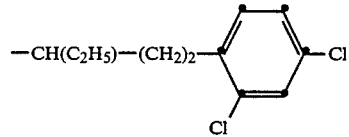

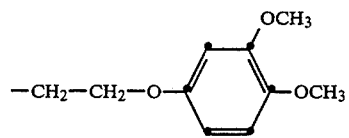

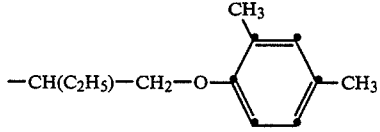

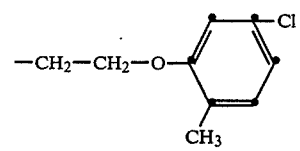

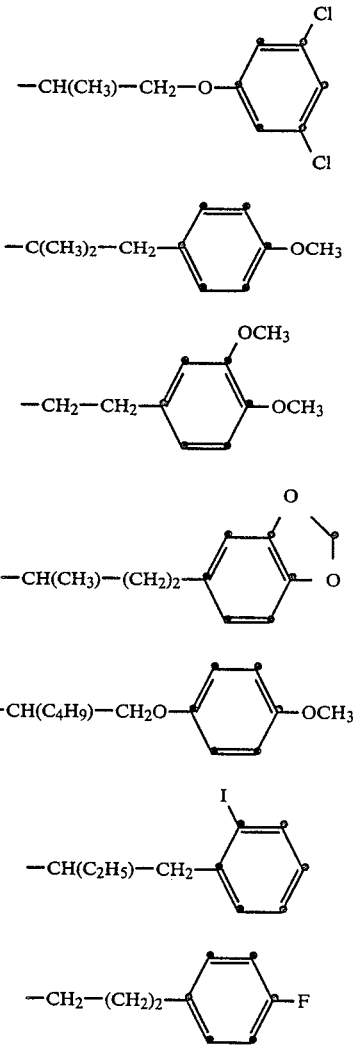

and the like.

The compounds of formula I have one chiral center at the 1-position in the aminoethanol substituent and can have a second chiral center when the $R_1$ and $R_2$ substituents in the R group are different. The chiral centers confer optical activity on the formula I compounds.

All the optical isomer forms, that is mixtures of enantiomers or diastereomers, e.g. racemates as well as individual enantiomers or diastereomers of formula I are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

A compound of Formula I is useful for treating glaucoma since it decreases intraocular pressure when topically administered to the eye. The ability to lower intraocular pressure is determined using an in-vivo protocol in a rabbit model.

Said compound is preferably administered in the form of an opthalmic pharmaceutical composition adapted for topical administration to the eye such as a solution, an ointment or as a solid insert. Formulations of the compound may contain from 0.01 to 5% and especially 0.5 to 2% of medicament. Higher dosages as, for example, about 10% or lower dosages can be employed provided the dose is effective in lowering intraocular pressure. As a unit dosage form, between 0.001 to 5.0 mg., preferably 0.005 to 2.0 mg., and especially 0.005 to 1.0 mg. of the compound is generally applied to the human eye.

The pharmaceutical composition which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols; vegetable oils; polyalkylene glycols; petroleum based jelly; ethyl cellulose; ethyl oleate; carboxymethylcellulose; polyvinylpyrrolidone; isopropyl myristate, and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000 bacterial components such as quaternary ammonium compounds, phenylmercuric salts known to have cold sterilizing properties and which are non-injurious in use, thimerosal, methyl and propyl paraben, benzyl alcohol, phenyl, ethanol, buffering ingredients such as sodium chloride, sodium borate, sodium acetate, glyconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water-soluble polymer as the carrier for the medicament. The polymer used to form the insert may be any water-soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates and as polyacrylic acid salts; natural products such as gelatin, alginates, pectins, tragacanth, karaya chondrus, agar, acacid; the starch derivatives such as starch acetate, hydroxyethyl starch ethers, hydroxypropyl starch, as well as other synthetic derivatives such as poly vinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert, is available in several polymeric forms, all of which are suitable in the preparation of these inserts. Thus, the product sold by Hercules, Inc. of Wilmington, Del., under the name KLUCEL, such as Klucel HF, HWF, MF, GF, JF, LF and EF, which are intended for food or pharmaceutical use, are particularly useful. The molecular weight of these polymers, useful for the purposes described herein, may be at least 30,000 to about 1,000,000 or more. Similarly, an ethylene oxide polymer having a molecular weight of up to 5,000,000 or greater, and preferably 100,000 to 5,000,000, can be employed. Further, for example POLYOX, a polymer supplied by Union Carbide Co., may be used, having a molecular weight of about 50,000 to 5,000,000 or more and preferably 3,000,000 to 4,000,000. Other specific polymers which are useful are polyvinyl pyrrolidine, having a molecular weight of from about 10,000 to about 1,000,000 or more, preferably up to about 350,000 and especially about 20,000 to 60,000; polyvinyl alcohol, having a molecular weight of from about 30,000 to 1,000,000, or more particularly about 400,000, and especially from about 100,000 to about 200,000; hydroxypropylmethyl cellulose, having a molecular weight of from about 10,000 to 1,000,000 or more, particularly up to about 200,000 and especially about 80,000 to about 125,000; methyl cellulose, having a molecular weight of from about 10,000 to about 1,000,000 or more, preferably up to about 200,000 and especially about 50 to 100,000; and CARBOPOL (carboxyvinyl polymer) of B. F. Goodrich and Co., designated as grades 934, 940 and 941. It is clear that for the purpose of this invention, the type and molecular weight of the polymer is not critical. Any water-soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer, which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye.

The insert can be of any suitable size to readily fit into the eye. For example, castings or compression molded films having a thickness of about 0.25 mm. to 15.0 mm. can be subdivided to obtain suitable inserts. Rectangular segments of the cast or compressed film, having a thickness between about 0.5 and 1.5 mm, can be cut to afford shapes such as rectangular plates of 4×5-20 mm or ovals of comparable size. Similarly, extruded rods having a diameter between about 0.5 and 1.5 mm can be cut into suitable sections to provide the desired amount of polymer. For example, rods of 1.0 to 1.5 mm in diameter and about 20 mm long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the terms smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from about 1 up to about 30% by weight. A particularly preferred plasticizer is water, which is present in amounts of at least about 5% up to about 40%. In actual practice, a water content of from about 10% to about 20% is preferred, since it may be easily accomplished and adds the desired softness and pliability to the insert.

When plasticizing the solid medicinal product with water, the product is contacted with air having a relative humidity of at least 40%, until said product picks up at least about 5% water and becomes softer and more pliable. In a preferred embodiment, the relative humidity of the air is from about 60% to about 99%, and the contacting is continued until the water is present in the product in amounts of from about 10% to about 20%.

Suitable water-soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water-soluble buffering agents are alkali, alkali earth carbonates, phosphates, bicarbonates, citrates, borates and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer. The insert may contain from about 1 mg. to 100 mg. of water-soluble polymer, more particularly from 5 to 50 mg. and especially from 5 to 20 mg. The medicament is present from about 0.1 to about 25% by weight of insert.

The ability of the Formula I compound to lower intraocular pressure is determined in rabbits with experimental glaucoma induced by intraocular injection of α-chymotrypsin. Compounds of Formula I are effective in lowering intraocular pressure after topical application. Pressure is reduced in the normal and the glaucomatous eye.

The compounds (Formula I) of the present invention have β-adrenergic blocking activity. This β-adrenergic blocking activity is determined by measuring the ability of representative compounds to block the β-adrenergic stimulant effect of isoproterenol in a test animal.

The compounds of the present invention also have α-adrenergic blocking activity. This α-adrenergic blocking activity is determined, (a) in vitro by measuring the ability of a representative Formula I compound to displace radio labeled α-adrenergic antagonist from a tissue substrate or (b) in vivo, by measuring the ability of representative Formula I compound to block the α-adrenergic stimulant effect of phenylephrine in anesthetized normotensive animals.

The present compounds exhibit antihypertensive activity of immediate onset. This rapid-onset antihypertensive activity is determined by administering a representative compound of the present invention to spontaneously hypertensive (SH) rats and measuring the effect on blood pressure.

The α- and β-adrenergic blocking activity of the present compounds indicates that the compounds may be useful in humans for reducing peripheral vascular resistance and treating cardiovascular conditions susceptible to β-blockade therapy (e.g., angina pectoris, arrhythmia), while minimizing bronchoconstriction via α-adrenergic blockage. This α/β-blocking effect can be useful in treating hypertension caused by pheochromocytoma.

For use as α/β-adrenergic blocking agents, and/or antihypertensive agents, the compounds of the present invention can be administered orally, by inhalation, by suppository or parenterally, i.e., intravenously, intraperitoneally, etc., and in any suitable dosage form. The compounds may be offered in a form (1) for oral administration, e.g., as tablets in combination with other compounding ingredients (diluents or carriers) customarily used, such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present compound) to compounding ingredients will vary as the dosage form required. Conventional procedures are used to prepare the pharmaceutical formulations.

The effective daily dosage level for the present compounds for cardiovascular applications may be varied from about 10 mg. to about 3000 mg. Daily doses ranging from about 100 to about 2500 mg. are preferred, with about 200 to about 1000 mg. being a more preferred range. Oral administration is preferred. Either single or multiple daily doses may be administered depending on unit dosage.

Compounds of Formula I also have bronchodilator activity. This is determined by measuring the effectiveness of the compound to antagonize slow reacting substance of anaphylaxis (SRS-A). Thus, the compounds may be useful to treat conditions in mammals, especially human beings, which benefit from bronchodilatation, such as asthma, etc. For use as a bronchodilator, the compound is administered orally or parenterally in conventional dosage form, such as tablet, capsule, solution, dispersion, emulsion and the like. The compound may also be administered as a spray or an aerosol, using an appropriate delivery device and formulation. The oral route is preferred.

Sufficient formula I compound is administered to produce the desired level of bronchodilation. Daily dosages for oral or parenteral administration may range from about 1 mg. to about 300 mg., and preferably from about 2 to about 150 mg. Spray or aerosol delivery will be in metered doses ranging from about 50 to about 1000 mcg., administered as needed.

Thus, other embodiments of the present invention are the pharmaceutical compositions containing a therapeutically effective amount of the Formula I compound and methods for treating the conditions indicated above.

Compounds of Formula I may be prepared by any convenient process. One such useful process is illustrated by the following reaction equation:

A. Process when $R^1$ is other than H

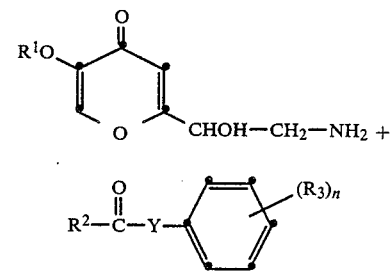

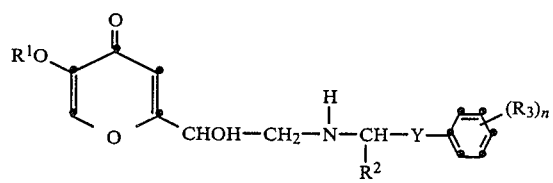

B. Process when $R^1$ is H

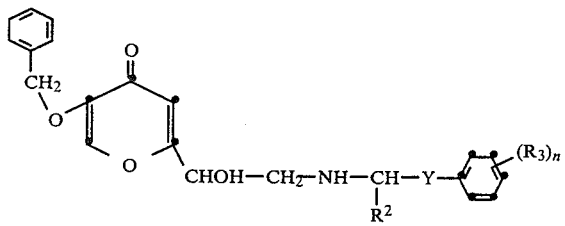

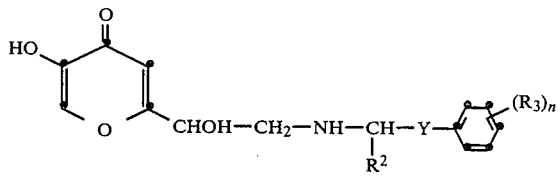

The following examples illustrate preparation of representative compounds for Formula I. All temperatures are in degree Celsius.

EXAMPLE 1

1-(5-Benzyloxy-4H-pyran-4-one-2-yl)-2-(1-methyl-3-phenylpropylamino) ethanol hydrochloride (A)

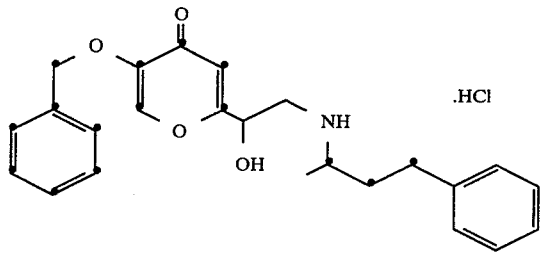

To 1-(5-Benzyloxy-4H-pyran-4-on-2-yl)-2-amino ethanol hydrochloride (1.94 g, 0.0065 m) and 3-phenyl-2-butanone (0.97 g, 0.0065 m) in methanol was added 65 ml of 0.1N NaOH followed by NaCN BH$_2$ (0.25 g, 0.004 m). The mixture was stirred for 2 days at room temperature after concentration, chromatography on silica gel 60 (E. Merck) eluting with 5% CH$_3$OH/CH$_2$Cl$_2$ saturated with NH$_3$ afforded the desired product as its free base. The hydrochloride salt was prepared by dissolving in ethanol and adding aqueous HCl. Filtration of the solid upon attempted ether extraction gave a poor yield of the desired salt A; m.p. 205°–208° C.

Claims to the invention follow.

What is claimed is:

1. A pharmaceutical composition for (a) reducing intraocular pressure (b) treating hypertension or (c) effecting bronchodilation containing an effective amount of a compound of the formula:

$$R^1O \begin{array}{c} O \\ \parallel \\ \end{array} \text{---CHOH---CH}_2\text{---NH---CH---Y---}(R_3)_n$$
$$\phantom{XXXXXXXXXXXXXXXXXXXX}|$$
$$\phantom{XXXXXXXXXXXXXXXXXXXX}R^2$$

racemates, diastereomers, individual isomers, tautomers, and pharmaceutically acceptable salts thereof, wherein $R^1$ is CH$_3$ or CH$_2$-phenyl
$R^2$ is H or C$_1$–C$_3$alkyl,
Y is CH$_2$, (CH$_2$)$_2$ or CH$_2$O,
$R_3$ is H, C$_1$–C$_3$alkyl, halogen, OH or OCH$_3$ and
n is 1 or 2
and a carrier.

2. A composition of claim 1 wherein Y is CH$_2$.
3. A composition of claim 1 wherein Y is (CH$_2$)$_2$.
4. A composition of claim 3 wherein R$_1$ is CH$_3$ and R$_2$ is H or CH$_3$.
5. A composition of claim 4 wherein R$_3$ is H or OCH$_3$.
6. A composition of claim 5 wherein the

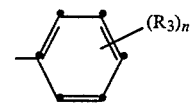

group is

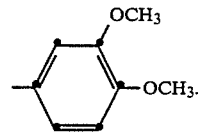

7. A composition of claim 1 wherein the formula A is

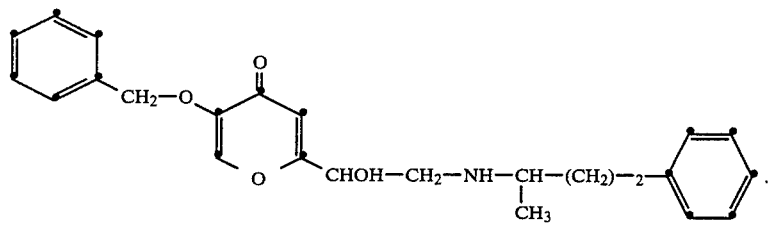

8. A method for (a) reducing intra-ocular pressure or (b) treating hypertension by administering an effective amount of a composition of claim 1.

* * * * *